United States Patent [19]

Nozaki et al.

[11] Patent Number: 5,024,938
[45] Date of Patent: Jun. 18, 1991

[54] RECOMBINANT DNA INSERTED WITH HEPATITIS B VIRUS GENE, MAMMALIAN CELLS TRANSFORMED WITH CLONED VIRAL DNA, AND PRODUCTION OF HEPATITIS B VIRUS PROTEINS

[75] Inventors: Chikateru Nozaki, Kumamoto; Atsushi Miyanohara, Neyagawa; Fukusaburo Hamada; Nobuya Ohtomo, both of Kumamoto; Kenichi Matsubara, Osaka, all of Japan

[73] Assignee: Juridical Foundation The Chemo-Sero-Therapeutic Research Institute, Kumamoto, Japan

[21] Appl. No.: 883,138

[22] Filed: Jul. 8, 1986

Related U.S. Application Data

[63] Continuation-in-part of Ser. No. 522,667, Aug. 12, 1983.

[30] Foreign Application Priority Data

Aug. 20, 1982 [JP] Japan .............................. 57-145092

[51] Int. Cl.[5] ............................................ C12P 21/00
[52] U.S. Cl. ................................. 435/68.1; 435/172.3; 435/69.1; 435/69.3; 435/320.1; 435/240.2; 935/1; 935/6; 935/10; 935/12; 935/32; 935/34; 935/60
[58] Field of Search ............. 435/172.3, 68, 70, 240.2, 435/320, 69.3

[56] References Cited

PUBLICATIONS

DuBois et al., PNAS USA, vol. 77, pp. 4549-4553, Aug. 1980.
Wain-Hobson et al., Chem. Abst. vol. 96:194427v, Jun. 7, 1982.
Lusky et al., Nature vol. 293, pp. 79-81, Sep. 3, 1981.
Wain-Hobson et al., Develop, Biol. Standard., vol. 50, pp. 293-300 (1982).
Liu et al., Eukanyotic Viral Vectons edited by Gluzman, CSH, pp. 55-60, Jun. 1982.
Southern et al., Eukanyotic Viral Vectons edited by Gluzman CSH, pp. 41-45, Jun. 1982.
Breitman et al., Mol. Cell. Biol., vol. 2, pp. 966-976, Aug. 1982.
Mulligan et al., Mol. Cell. Biol., vol. 1, pp. 449-459, May 1981.

Primary Examiner—Elizabeth C. Weimar
Assistant Examiner—Suzanne Ziska
Attorney, Agent, or Firm—Wegner, Cantor, Mueller & Player

[57] ABSTRACT

A recombinant DNA comprising 3 fragments of Hepatitis B virus DNA recombined with a vector consisting essentially of 0.31 Kb replication orgin of SV40 DNA inserted into EcoRI cleavage site of *Escherichia coli* plasmid which is deficient in the 1.426-2.521 Kb region of inhibiting replication in mammalian cells, wherein each HBV DNA fragment is a 3.2 Kb BamHI fragment consisting of 1.9 Kb HBc gene and 1.3 Kb HBs gene, and said HBV DNA fragments are arranged in a head-to-tail tandem relationship wherein the HBc gene positions at the head and the HBs gene positions at the tail, mammalian cells transformed with the recombinant DNA, and a method of production of Hepatitis B virus proteins, i.e. HBsAg and/or HBeAg. These HBV proteins have the same immunological properties as those of the natural HBV proteins originated from human blood plasma and can be used for the preparation of HBV vaccine and diagnostic reagents.

8 Claims, 3 Drawing Sheets

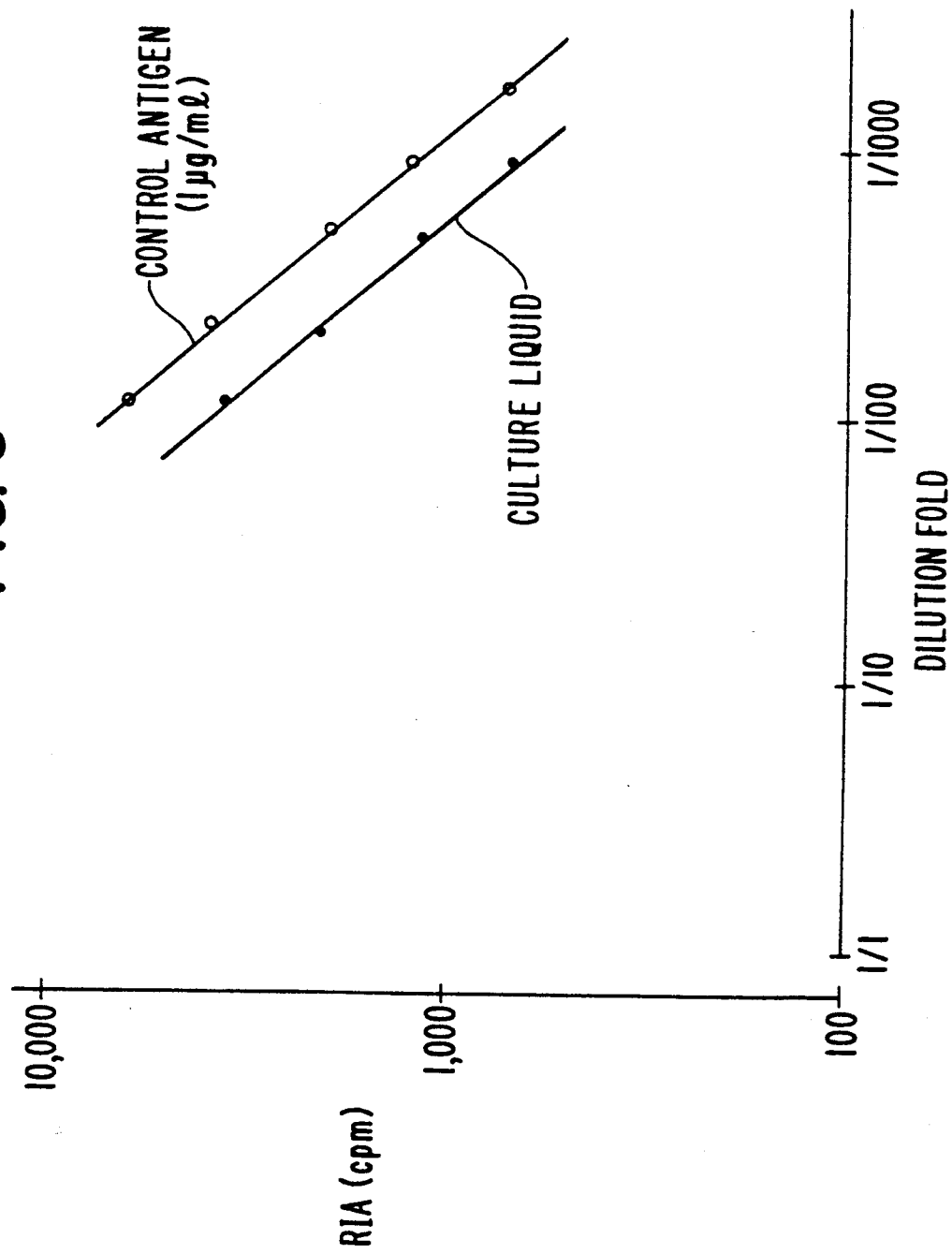

RECOMBINANT DNA INSERTED WITH HEPATITIS B VIRUS GENE, MAMMALIAN CELLS TRANSFORMED WITH CLONED VIRAL DNA, AND PRODUCTION OF HEPATITIS B VIRUS PROTEINS

CROSS-REFERENCE TO RELATED APPLICATION

This is a Continuation-in-part application of U.S. Ser. No. 522,667 filed on Aug. 12, 1983, abandoned.

TECHNICAL FIELD OF THE INVENTION

The present invention relates to a recombinant DNA inserted with hepatitis B virus genes which is suitable for transforming mammalian cells, mammalian cells transformed therewith, and a method for the production of hepatitis B virus proteins. More particularly, it relates to an industrial production of hepatitis B virus (hereinafter, referred to as "HBV") proteins, which comprises producing a novel recombinant DNA inserted with HBV genes by using a plasmid vector, transforming mammalian cells with the recombinant DNA, and culturing the transformed mammalian cells.

TECHNICAL BACKGROUND AND PRIOR ART

Hepatitis B, which is usually caused by transfusing blood of HBV positive patient or others, is hardly remedied, and there is no drug suitable for complete remedy thereof. Most suitable prophylaxis is a vaccine consisting of HBV surface antigen (hereinafter, referred to as "HBs antigen", "HBsAg" or "s antigen"). However, it is very difficult to produce the HBsAg vaccine on an industrial scale, because HBV is infectious only to human subjects and chimpanzee (it has never been successful to make a cell culture infected with HBV), and owing to this specificity of HBV, HBsAg must be obtained only from human blood serum.

It has recently been proposed to prepare HBsAg by *E. coli* with recombinant DNA instead of using human blood serum (cf. Japanese Patent Laid Open Application No. 104887/1980). However, according to this method using *E. coli*, it is still difficult to produce the desired HBsAg on an industrial scale, because the produced HBsAg is easily decomposed within the cells of *E. coli* and further growth of *E. coli* is inhibited by the produced HBsAg, which results in less productivity of HBsAg.

It has also been proposed to transform a certain animal cells with a cloned DNA (cf. Japanese Patent Laid Open Application No. 39784/1982). However, the recombinant DNA used in this method is prepared by inserting HBV DNA into *E. coli* plasmid pBR322, said plasmid pBR322 being not subjected to deletion of the site of inhibiting replication in mammalian cells and to insertion of a DNA (e.g. SV40 DNA) which can replicate in mammalian cells, and hence, when this recombinant DNA is introduced into mammalian cells, for instance monkey cells (e.g. COS Cells, cf. Gluzman, Y.; Cell, 23, 175–182, 1981), it can not effectively be grown in the cells, and further there is produced only HBs antigen with avoiding the production of HBe antigen.

It is also known to use SV40 DNA as a vector for preparing a recombinant DNA wherein a rabbit β-globulin gene is inserted (cf. Y. Takagi, et al, "Procedure for Experiment in Genetic Engineering", Third Ed., published by Kodansha, July 1, 1981, pages 122–125), but in this method, the SV40 DNA is a long fragment containing also the promoter region and the resultant recombinant DNA is directly inserted into mammalian cells which are infected thereby together with a helper SV40 mutant DNA to produce viral particles.

Furthermore, it is known that HVB proteins are produced by a recombinant DNA comprising an HBV fragment recombined with SV40 DNA vector (cf. Japanese Patent Laid Open Application No. 56685/1983 = U.S. Ser. No. 298,235 and Japanese Patent Laid Open Application No. 995/1983 = U.S. Ser. No. 249,352). However, in these invention, the SV40 DNA vector is a long fragment containing also the promoter region like above and the produced proteins comprise mainly HBs antigen, and it can not produce the protein on a large scale.

BRIEF SUMMARY OF THE INVENTION

The present inventors have extensively studied on an improved method for producing HBV proteins on an industrial scale by using novel transformed mammalian cells. As a result, it has been found that a novel recombinant DNA which is suitable for transforming mammalian cells can be prepared by inserting HBV gene into a recombinant DNA which can replicate in both *E. coli* and COS cells, and that there can be produced the desired HBV proteins having the same immunological properties as those of natural HBV proteins origined from human blood serum on an industrial scale by using mammalian cells transformed with said novel recombinant DNA.

An object of the present invention is to provide a novel recombinant DNA inserted with HBV gene which is suitable for transforming mammalian cells. Another object of the invention is to provide mammalian cells transformed with the recombinant DNA, particularly transformed COS cells and mouse L cells. A further object of the invention is to provide a method for producing HBV proteins on an industrial scale by using said transformed mammalian cells. These and other objects and advantages of the invention will be apparent to persons skilled in the art from the following description.

BRIEF DESCRIPTION OF THE DRAWING

FIG. 5 is a graph showing relation between the amount of antigen [activity in Radioimmunoassay (RIA)] and the dilution fold in the culture liquid of the transformed mammalian cells of this invention, wherein the data as to control antigen are also shown.

DETAILED DESCRIPTION OF THE INVENTION

The novel recombinant DNA of the present invention can be prepared by inserting HBV genes into a vector, e.g. pXRIIG (cf. Lusky, M., Nature 293, 79, 1981). Said novel recombinant DNA can be used for transforming mammalian cells, preferably thymidine kinase deficient (TK−) mammalian cells (e.g. mouse LTK− cells). The present invention is characteristic in that there are produced as the HBV proteins not only HBs antigen but also HBe antigen (hereinafter, referred to as "HBeAg" or "e antigen") which has never been isolated.

The production of the recombinant DNA, transformed mammalian cells, and HBV proteins are illustrated below in more detail.

(1) HBV gene

Figure 1:
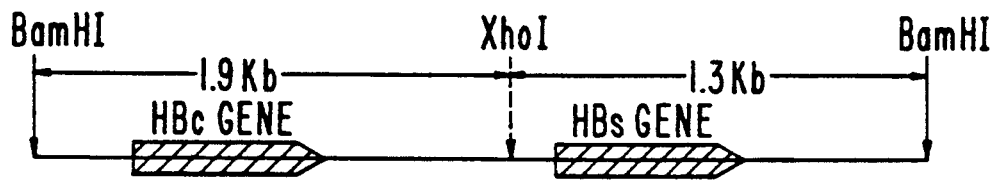
FIG. 1 shows a structure of each fragment of the HBV DNA used in this invention which is recombined with the SV40 DNA vector and has BamHI site at both terminals.

The HBV gene is an HBV DNA of subtype adr which is frequently observed in Japan and also in countries of Southeast Asia and is cloned by $E.\ coli$. The HBV gene contains each one recognition site of restriction enzymes XhoI and BamHI. This fragment, e.g. a fragment having an BamHI site at both terminals which is obtained by digesting with BamHI has a structure as shown in the accompanying FIG. 1, wherein HBs gene and HBc gene are present in the same direction and the HBc gene positions at the head and the HBs gene positions at the tail.

The HBV DNA is prepared in the following manner.

Viral particles (Dane particles) are isolated from blood of a person having HBe antigen by a conventional method. The HBV DNA (3,200 bp) usually has a double-stranded circular structure, but about 15 to 50% regions thereof show single-strand. Accordingly, in order to change the single-stranded regions to double-strand suitable for cloning the gene, it is treated with an endogenous DNA polymerase by the method of Sattler and Robinson (cf. F. Sattler & W. S. Robinson, Journal of Virology, 32, 226–233, 1979, "Hepatitis B viral DNA molecules have cohesive ends"). After repairing all regions into double-strand, the DNA is extracted, and amplified by cloning by $E.\ coli$, and then treated with an appropriate restriction enzyme to give a fragment which is used for construction of the desired plasmid.

The HBV DNA is preferably of subtype adr which is frequently observed in Japan and in other countries in Southeast Asia, but may be HBV of subtype adw and ayw which are frequently observed in European countries and U.S.A.

(2) Vector

The vector used in the present invention consists of an $E.\ coli$ plasmid inserted with a replication origin of SV40 DNA, which can replicate in both $E.\ coli$ and mammalian cells. The $E.\ coli$ plasmid includes any conventional plasmids, for example, originated from ColEl, pMBl (cf. Hershfield, V., Proc. Natl. Acad. Sci, U.S.A., 71, 3455, 1974) and plasmid originated from p15A (cf. Chang, A.C.Y., J. Bact., 134, 1141, 1978).

The SV40 DNA to be inserted into $E.\ coli$ plasmid is a DNA of a virus which is well known as a mammalian cancer virus being capable of infecting and inducing a cancer in monkeys. The SV40 DNA is usually used in genetic engineering industries by recombining it with other DNA, for instance, recombining with β-globin gene, and introducing the recombinant DNA thus obtained into monkey culture cells to produce β-globin (cf. Mulligan, R. C., Nature 277, 108, 1979). In the present invention, the replication origin of the SV40 DNA (it is usually referred to as "SV40 ori") is inserted into an $E.\ coli$ plasmid and then is used in the preparation of recombinant DNA with HBV gene. The recombinant DNA thus prepared can replicate in both $E.\ coli$ and COS cells.

Figure 2:
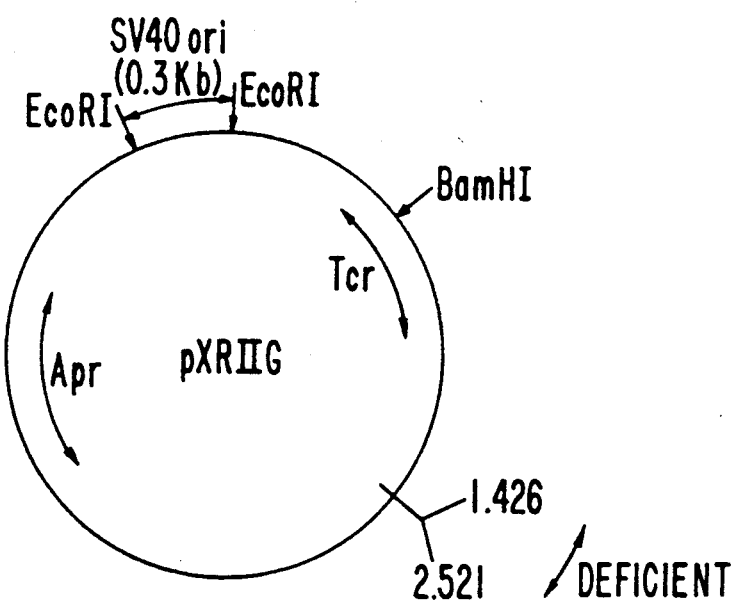
FIG. 2 shows a structure of SV40 DNA "pXRIIG" used as a vector in this invention which consists essentially of 0.31 Kb replication origin of SV40 DNA inserted into EcoRI cleavage site of *E. coli* plasmid pBR322 which is deficient in the 1.426–2.521 Kb region of inhibiting replication in mammalian cells.

The vector used in the present invention is preferably deficient in the replication-inhibiting region. Preferred example of such a DNA is a recombinant DNA consisting of $E.\ coli$ plasmid pBR 322 deficient in region toxic to mammalian cells (i.e. region of inhibiting replication within COS cells; 1.426–2.521 kb) (said plasmid pBR322 being designated "pXf³") and a replication origin (0.31 kb) of SV40 DNA. The recommbinant DNA is designated "pXRIIG" and has a structure as shown in the accompanying FIG. 2. As is shown in FIG. 2, the replication origin (0.31 kb) of SV40 DNA is inserted into EcoRI cleavage site of pBR322, and the recombinant DNA is deficient in the region (1.426–2.521 kb) of inhibiting replication in mammalian cells and optionally deficient also in other unnecessary region (e.g. 3.102–3.211 kb) in order to shorten the size of vector, and said recombinant DNA contains a tetracycline-resistant gene ($Tc^r$) and an ampicillin-resistant gene ($Ap^r$). These antibiotics resistant genes are useful as a selective marker in the preparation of transformed $E.\ coli$ and include other various antibiotics resistant genes, such as kanamycin-resistant gene, chloramphenicol-resistant gene, etc.

The vector is used for the preparation of a recombinant DNA with an HBV gene in the form of a fragment after being cleaved with BamHI.

(3) Construction of recombinant DNA (HBV gene-expression plasmid)

Figure 3:
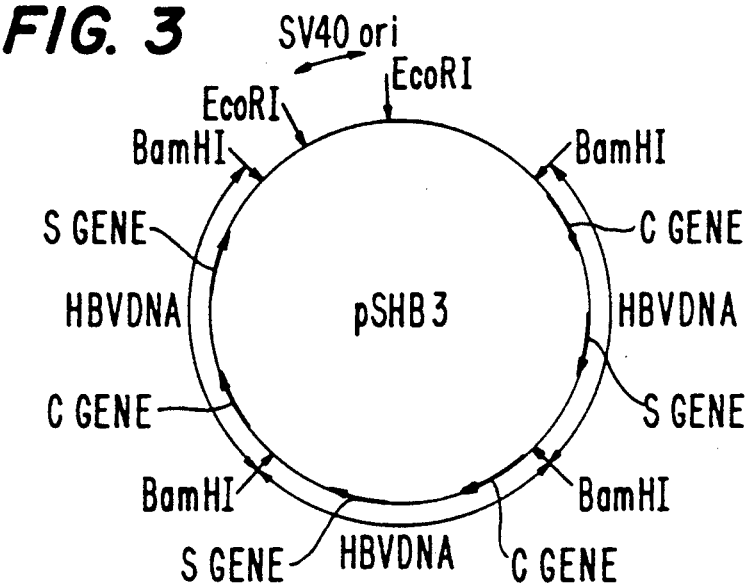
FIG. 3 shows one embodiment of a recombinant DNA obtained by this invention which consists of three BamHI fragments of HBV DNA and one fragment of the vector.

A fragment obtained by digesting the above vector with an appropriate restriction enzyme (e.g. BamHI) is recombined with a fragment containing an HBV gene in an appropriate ratio to give the desired recombinant DNA. By varying the ratio of each fragment, there can be obtained various recombinant DNAs wherein one fragment of the vector is preferably inserted into two to four fragments of HBV DNA. Usually, the fragment of vector and the fragment of HBV DNA are used in the ratio of 1:2 to 1:10 by mole. One embodiment of the recombinant DNAs has a structure as shown in the accompanying FIG. 3, which is a recombinant DNA consisting of three BamHI fragments of HBV DNA and one fragment of the vector (designated "pSHB3"). As is shown in FIG. 3, the HBV DNA fragments are inserted in the same direction, i.e. in the head-to-tail tandem form, wherein the HBc gene positions at the head and the HBs gene positions at the tail.

(4) Transformation of mammalian cells

The above recombinant DNA inserted with HBV genes is introduced into mammalian cells together with TK genes and then culturing it to transform the mammalian cells.

The mammalian cells are preferably TK− cells, e.g. mouse LTK− cells, because only the desired transformed cells can selectively be isolated, while the transformation is carried out by treating the cells with the recombinant DNA together with several tens to several hundreds times of TK genes. There may also be used a recombinant DNA inserted with TK genes instead of using together the recombinant DNA and TK genes.

The recombinant DNA can also be introduced into other mammalian cells, for example into COS cells in which the pXRIIG can replicated, and the desired HBsAg is produced by culturing the transformed COS cells.

The transformation is more specifically illustrated below in the case of using mouse LTK⁻ cells as the mammalian cells.

Mouse LTK⁻ cells are cultured in a Dulbecco's modified Eagle medium (hereinafter, referred to as "DMEM") supplemented with 10% calf serum (cf. Dulbecco, R. & Freeman, G.; Virology, 8, 396, 1959) and thereto is added a solution of the recombinant DNA and TK gene in an aqueous calcium phosphate solution, and the mixture is allowed to stand at room temperature for a few or several tens of minutes, usually for about 30 minutes. To the resulting mixture is added additional DMEM, and the mixture is cultured for 4 to 5 hours. After substituting new DMEM, the mixture is further cultured for 12 to 24 hours. The resulting culture is further cultured in a medium containing hypoxanthine (15 μg/ml), aminopterin (1 μg/ml) and thymidine (5 μg/ml) (hereinafter, referred to as "HAT medium") [cf. Littlefield; J. Proc. Natl. Acad. Sci. USA, 72, 3961-3965, 1963] to give the desired transformed mouse L cells. In the above transformation procedure, the starting mouse LTK⁻ cells are deficient in TK gene and hence can not grow in HAT medium, but on the other hand, the transformed mouse L cells inserted with TK gene is capable of synthesis of thymidine kinase and hence can grow in HAT medium. Accordingly, only the desired transformed cells can selectively be isolated by culturing in the above HAT medium.

(5) TK gene

Figure 4:
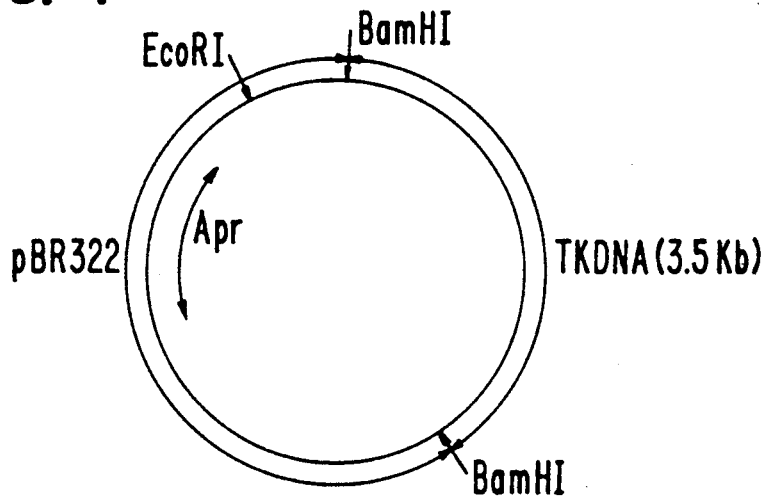
FIG. 4 shows a structure of a recombinant DNA of an *E. coli* pBR322 plasmid and a TK gene derived from herpes simplex virus, which is used in the transformation of mammalian cells together with the recombinant DNA of this invention.

The TK genes are used in the above transformation of mammalian cells together with a recombinant DNA inserted with an HBV gene. The TK gene is a recombinant DNA of an *E. coli* plasmid (e.g. pBR322) and a TK gene derived from herpes simplex virus and has a structure as shown in the accompanying FIG. 4 [cf. Florence Colbere-Garapin, 3rd General Meeting of ESACT, Oxford 1979, Develop. biol. Standard, 46, 75–82, 1980].

(6) Culture of transformed mammalian cells and production of HBV protein

The transformed mammalian cells obtained above are cultured in an appropriate medium in a usual manner to produce a large amount of HBV proteins, not only "s" antigen but also "e" antigen, within the grown cells, which are released into the medium. In this culture, a mixture of "s" antigen and "e" antigen is produced, but they can easily be separated by a conventional purification method of proteins, for instance, by passing the culture broth through a column packed with an anti-HBs antibody and then eluting the "s" antigen with a 0.1 M HCl-glycine buffer, and likewise by passing the culture broth through a column packed with an anti-HBe antibody and then eluting the "e" antigen therefrom with the same buffer as above.

The HBV proteins thus obtained have the same immunological properties as those of the natural HBV proteins originated from human blood serum and can be used for the preparation of HBV vaccine and diagnostic reagents like the natural HBV proteins.

The recombinant DNA, transformed mammalian cells and production of HBV proteins of the present invention are illustrated by the following examples, but should not be construed to be limited thereto.

EXAMPLE 1

(1) Preparation of HBV DNA (i) Preparation of virus DNA

A pooled blood plasma (700 ml) obtained from ten persons who are positive in HBsAg (subtype adr) and HBeAg is centrifuged at 5,000 r.p.m. for 20 minutes to remove undissolved materials. The resulting solution is centrifuged at 4° C., 18,000 r.p.m. for 8 hours, and the resultant precipitates are re-dissolved in 10 ml of a buffer (pH 7.5) of 10mM Tris-HCl, 0.1 M NaCl and 1 mM EDTA. The solution is added to the top of a centrifugal tube containing 30% sucrose, which is centrifuged at 4° C., 39,000 r.p.m. for 4 hours. The resultant precipitates are re-dissolved in the same buffer as above.

In order to make easier the following operation, the buffer solution is subjected to the reaction by HBV DNA polymerase by treating it in a mixture (500 μl) of 67 mM Tris-HCl (pH 7.5), 80 mM NH₄Cl, 25 mM MgCl₂, 0.5% NP40 (Tergitol, manufactured by Sigma Co.), 0.1% 2-mercaptoethanol, 330 μM dCTP (deoxycytidine triphosphate), dGTP (deoxyguanosine triphosphate), and dATP (deoxyadenosine triphosphate), 0.5 μM α-[³²P] dTTP (deoxythymidine triphosphate) at 37° C. for 3 hours, and to the reaction mixture is added the same volume of 100 mM EDTA solution. By the above DNA polymerase reaction, single-stranded region of the DNA is repaired to wholly double-strand to give a [³²P] labeled material. This material is added to the top of a centrifugal tube wherein 30%, 20% and 10% aqueous solutions of sucrose are packed in layers in this order, and it is centrifuged at 4° C., 39,000 r.p.m. for 4.5 hours.

In order to digest the proteins strongly bonded to DNA, the precipitates obtained above are treated in a mixture (200 μl) of 1 mg/ml of pronase E (manufactured by Kaken Kagaku K.K., Japan) and 0.2% aqueous sodium laurate solution at 37° C. for 2 hours. The resulting mixture is extracted with phenol (200 μl) twice, and the resulting DNA-containing extract is washed with ether to remove phenol solvent to give a solution of HBV DNA. The DNA thus obtained has a specific radioactivity of $2.5 \times 10^6$ cpm/μg and can be used for digestion with restriction enzymes.

(ii) Cloning of HBV DNA

The double-stranded circular HBV DNA obtained above is cloned by using λ-phage Charon 16A DNA as a vector and then is again cloned by using the known plasmid pBR322 as a vector as follows.

(A) Cloning in the system of λ-phage Charon 16A host-vector:

HBV DNA (20 ng) is treated with endonuclease XhoI in a mixture (20 μl) of 10 mM Tris-HCl (pH 7.4), 7 mM MgCl₂, 100 mM NaCl and 7 mM 2-mercaptoethanol at 37° C. for 2 hours. The resulting mixture is extracted with phenol (20 μl) and further with ether, and to the aqueous layer is added double volume of cooled ethanol to precipitate DNA. The mixture is kept at −70° C. for one hour and then centrifuged at 10,000 r.p.m. for 5 minutes, and the precipitated DNA is recovered. The precipitates thus separated are dissolved in a mixture (5 μl) of 10 mM Tris-HCl (pH 7.4) and 1 mM EDTA. The HBV DNA and an equimolar amount of λ-phage Charon 16 A DNA (having one recognition site of XhoI) obtained by cleavage with endonuclease XhoI like above are reacted with T4 DNA ligase [a mixture of 50 mM Tris-HCl (pH 7.4), 10 mM MgCl₂, 10 mM dithiothreitol, 100 μg/ml calf serum albumin, 0.5 mM ATP and 0.5 μl enzyme preparation (T4 ligase, manufactured by Takara Biomedicals, Japan, $1-5 \times 10^3$ unit/ml)] at 4° C. for 18 hours. The reaction mixture is extracted with phenol and ether and then subjected to precipitation with ethanol in the same manner as described above. The precipitates thus obtained are dissolved in a mixture (10 μl) of 10 mM Tris-HCl (pH 7.4) and 1 mM EDTA.

The thus annealed DNA is subjected to an in vitro packaging operation to form λ-phage in the same manner as described in "Methods in Enzymology", 68, 299–309 and further plaques ($10^4$) are formed therefrom on an L-agar plate (23 cm×23 cm) by using *E. coli* DP50 SupF (cf. Blatter, F. R., Science 196, 161, 1977) as an indicator. These plaques are subjected to plaque hybridization using $^{32}$P-labeled HBV DNA prepared above as a probe (cf. Science, 196, 180, 1977) in order to select plaques formed from the phage having HBV DNA, by which a plural of the desired phages are separated.

(B) Re-cloning by using plasmid pBR322 as a vector:

From the phage having HBV DNA obtained in the above (A), a phage DNA is prepared by using *E. coli* DP50-SupF as a bacteria to be infected in the same manner as described in "Methods in Enzymology", 68, 245–378, 1979. The DNA thus obtained is digested with XhoI under the same conditions as described above for 2 hours, and the resulting reaction mixture is subjected to an electrophoresis with 0.75% agarose gel to isolate HBV DNA (3.2 kb). The HBV DNA is absorbed onto DEAE (diethylaminoethyl cellulose) paper (manufactured by Toyo Roshi, Japan) in order to separate from the vector DNA and then is eluted with 1 M NaCl aqueous solution. The HBV DNA thus obtained is treated with T4 ligase under the same conditions as described above to give a circular HBV DNA (3.2 kb). This HBV DNA is treated with BamHI to give a BamHI fragment of HBV DNA.

Separately, *E. coli* pBR322 having a single BamHI cleavage site within tetracycline-resistant gene thereof is digested with BamHI, and the product is purified by phenol extraction and ethanol precipitation in the same manner as described above.

The thus obtained pBR322 cleaved with BamHI is mixed with BamHI fragment of HBV DNA obtained above in a molar ratio of 1:5, and the mixture is annealed with T4 DNA ligase for 18 hours as described above.

The annealed DNA preparation (10 μl) obtained above is added to a liquid of *E. coli* (0.1 ml) which is prepared by treating a culture broth of *E. coli* χ1776 (cf. Curtiss, R. III, "Molecular Cloning of Recombinant DNA" ed. Scott, W. A. and Werner, R., page 99, Academic Press, 1977) by the procedure as described in Norgard, M. V., Gene, 3, 279 (1978), and the mixture is mixed well and allowed to stand at 0° C. for 25 minutes. The mixture is applied onto an L-agar plate containing ampicillin (20 μg/ml), α-biotine (1 μg/ml), diaminopimelic acid (100 μg/ml) and thymine (20 μg/ml) and is incubated at 37° C. overnight. The resulting colonies are applied onto both an agar plate containing tetracycline (20 μg/ml) and an agar plate containing ampicillin (20 μg/ml), and the colonies which grow only on the agar plate containing ampicillin is selected. pBR322 has an ampicillin-resistant gene and a tetracycline-resistant gene, but when it is inserted with HBV DNA at the BamHI site of the tetracycline-resistant gene, it loses the tetracycline-resistance. Accordingly, the selected colonies have a recombinant DNA of pBR322-HBV DNA. From the colonies thus selected, a plasmid is prepared by the procedure as described by K. Matsubara (cf. J. Virol., 16, 479, 1975). The plasmid thus obtained, i.e. the recombinant DNA of pBR322-HBV DNA linked at the BamHI site), is treated with BamHI under the same conditions as described above, and the reaction mixture is subjected to an electrophoresis with 0.75% agarose gel in the same manner as described above to give a BamHI fragment of HBV DNA.

(2) Preparation of vector (pXRIIG BamHI fragment)

A vector pXRIIG is prepared as follows.

SV40 DNA (10 μg) is cleaved with EcoRII in a mixture of 50 mM Tris-HCl (pH 8.0), 50 mM NaCl, 5 mM MgCl$_2$, and 1 mM dithiothreitol. The reacture mixture is subjected to an electrophoresis with 1% agarose gel, and 311 bp fragment of EcoRIIG containing a replication initiation region of SV40 is isolated. The DNA fragment (1 mole) thus obtained is linked with EcoRI linker (about 10 mole) by T4 DNA ligase in a mixture of 50 mM Tris-HCl (pH 7.4), 10 mM MgCl$_2$, 10 mM dithiothreitol, 0.5 mM ATP and 100 μg/ml calf serum albumin. After extraction with phenol and precipitation with ethanol, the product is cleaved with EcoRI in a mixture of 50 mM Tris-HCl (pH 7.5), 7 mM MgCl$_2$, 100 mM NaCl, and 7 mM 2-mercaptoethanol. After extraction with phenol and precipitation with ethanol, the product is mixed with pBR322 (which is previously cleaved with EcoRI) (10:1 by mole) and treated with T4 DNA ligase. *E. coli* χ1776 is transformed with the above reaction mixture, and the transformants are selected on an agar medium containing ampicillin. From the transformants, there is obtained a plasmid pSV01 in which 311 bp fragment of SV40 DNA is inserted at EcoRI site of pBR322 (cf. Proc. Natl. Acad. Sci. U.S.A., Vol. 77, 6491, 1980).

pSV01 thus obtained is cleaved with PvuII in a mixture of 10 mM Tris-HCl (pH 7.5), 7 mM MgCl$_2$, 60 mM NaCl, and 7 mM 2-mercaptoethanol, and then subjected to extraction with phenol and precipitation with ethanol. The resulting product is reacted with exonuclease Bal 31 in a mixture of 20 mM Tris-HCl (pH 8.0), 12 mM CaCl$_2$, 12 mM MgCl$_2$, 1 mM EDTA, and 600 mM NaCl. After extraction with phenol and precipitaiton with ethanol, the product is reacted with T4 DNA ligase. *E. coli* χ1776 is transformed with the above reaction mixture, and the transformants are selected on an agar medium containing ampicillin, from which there is obtained plasmid pXRIIG which is deficient in the region of inhibiting replication in mammalian cells (cf. Nature, Vol. 293, 79, 1981).

The vector pXRIIG (1 μg) as prepared above is added to a mixture (20 μl) of 10 mM Tris-HCl (pH 8.0), 7 mM MgCl$_2$, 100 mM NaCl and 2 mM 2-mercaptoethanol, and thereto is added one unit of BamHI (one unit: an enzymatic activity being capable of completely digesting 1 μg of λ-DNA per one hour), and the mixture is reacted at 30° C. for one hour. The reaction mixture is extracted with phenol, and the aqueous layer is extracted with ether and then subjected to ethanol precipitation. The precipitates are dissolved in water, which is used in the preparation of a recombinant DNA.

(3) Preparation of a recombinant DNA of HBV DNA-pXRIIG

A solution (50 μl) containing HBV DNA BamHI fragment (150 ng) and pXRIIG BamHI fragment (50 ng) is reacted with T4 DNA ligase at 16° C. for 4 hours.

*E. coli* χ1776 is transformed with the reaction mixture obtained above in the same manner as described above. From the resulting transformants, there are selected colonies which grow on an agar medium after incubating on L-agar plate for 12 hours in the same manner as described in the above (1), (B), and the colonies thus selected are applied onto an agar medium containing tetracycline (Tc) (10 μg/ml) and an agar medium containing ampicillin (Ap) (40 μg/ml). The colonies (clones) which can not grow on the Tc-containing agar medium but can grow on the Ap-containing agar medium are selected. These clones are each incubated in the culture liquid of *E. coli* χ1776 as mentioned above, and the plasmids are extracted in the same manner as described above. By analysis of the cleavage pattern with various restriction enzymes (e.g. BamHI, XhoI, Hind III, Sal I), there is selected a recombinant DNA consisting of three BamHI fragments of HBV DNA and one fragment of pHRIIG (said recombinant DNA being designated pSHB3).

(4) Transformation of mammalian cells

The following liquid A and liquid B are prepared.

Liquid A: a solution (1.25 ml, pH 7.1) consisting of 50 mM Hepes (i.e. N-2-hydroxyethylpiperazine-N-2-ethanesulfonic acid), 280 mM NaCl, and 15 mM $Na_2HPO_4$ 12 $H_2O$.

Liquid B: a mixture of DNA solution (1.1 ml) consisting of pSHB3 (50 μg), pTK (2.5 μg) (cf. Colbere-Garapin, F., Proc. Natl. Acad. Scie. USA, 76, 3755, 1979), salmon spermatic DNA (carrier DNA) (50 μg) and 0.24 M $CaCl_2$.

The liquid B is added dropwise with stirring to the liquid A, and the mixture is allowed to stand at room temperature for 30 minutes. After pipetting sufficiently, the mixture (0.5 ml) is added dropwise to a single layer of mouse LTK$^-$, cells (about $10^5$ cills/flask) in a flask. The flask is kept at room temperature for 30 minutes in order to make the mixture absorbed into the cells, and thereto is added DMEM (5 ml), and the mixture is incubated under 5% $CO_2$ at 37° C. for about 5 hours. After exchanging with new DMEM, the mixture is further incubated for about 24 hours, and then, the medium is exchanged to HAT medium. The incubation is continued while the medium is exchanged with a new HAT medium every two to three days. After 4 weeks, the colonies of cells of TK$^+$ are collected to give the desired transformed cells.

In the case of using COS cells as the mammalian cells, the transformation is done by the method described as above with the exception that the TK gene is omitted in the B solution and that the culture medium is not required to change to HAT medium any more.

(5) Production of HBV proteins

The culture liquid of the transformed mouse L cells (LTK$^+$) obtained in the above (4) is detected with a kit for detecting HBsAg, HBeAg and HBcAg (manufactured by Abbott, U.S.A.). As a result, HBsAg and HBeAg are detected, but HBcAg is not detected.

As to the culture liquid obtained above, the reactivity and amount of antigen are assumed in accordance with a parallel line assay using a kit for detecting HBsAg as above (cf. Finney, D. J., "Statistical method in biological assay, 2nd edn. Griffin, London, 1964), wherein purified HBsAg obtained from human blood serum is used as a control antigen. The results are shown in the accompanying FIG. 5. As is clear from FIG. 5, the amount of antigen in the culture liquid of the transformed mouse cells is 600 ng/ml. Moreover, from based on the parallelism with the control antigen, it is also clear that the HBsAg produced by the present invention has similar reactivities (antigenicity, immunogenicity, etc.) to those of HBsAg present in human blood plasma.

To the culture liquid (5 ml) obtained above is added cesium chloride (1.5 g), and the mixture is centrifuged at 4° C., 200,000 × g for 60 hours, and fractions having maximum antigenicity of HBsAg and HBeAg are separated. When the specific gravity of these fractions is measured, the fraction having maximum antigenicity of HBsAg has a specific gravity of about 1.20 and the fraction of HBeAg has that of about 1.28, which are almost the same as those of HBsAg and HBeAg present in human plasma, respectively.

Besides, the transformed cells are set with carbon tetrachloride at 4° C. for 30 minutes and reacted with rabbit anti-HBs anti-serum (as the primary antibody), followed by washing and drying, and then is reacted with a fluorescent pigment-labeled anti-rabbit IgG antibody (as the secondary antibody), followed by washing and drying. The resulting cells are observed with fluorescent microscopy. As a result, there is observed a specific fluorescence within the cytoplasm of the transformed cells.

The culture liquid (100 μl) obtained above is reacted with rabbit anti-HBs antibody (antibody value PHA $2^8$) (100 μl) at room temperature for 12 hours and the reaction mixture is centrifuged at 10,000 × g for 30 minutes. The resulting precipitates are stained with uranyl acetate and observed with an electron microscope. As a result, there are observed numerous aggregated images of particles (particle size 22 nm) similar to HBsAg particles present in human plasma which is treated likewise, but there are not observed any tubular particles or Dane particles (HBV).

Thus, the transformed mouse L cells produce and release HBsAg and HBeAg in the medium.

The HBsAg and HBeAg thus produced are isolated from the culture liquid in the following manner.

The culture liquid (100 ml) is passed through a column packed with guinea pig anti-HBs antibody carried on Sepharose CL 4B (manufactured by Pharmacia, Sweden), by which only HBsAg is adsorbed thereon, and hence, the HBsAg is isolated by eluting it with 0.1 M HCl-glycine buffer (pH 2.5).

The HBsAg thus obtained was subcutaneously inoculated to guinea pigs (female, 300–400 g, 10 animals) once a week for three weeks and further one time after one month therefrom, and the antibody in blood plasma was measured with a kit for detecting anti-HBs antibody (AUSAB, manufactured by Abbott, U.S.A.). As a result, there was observed in all animals the increased antibody value as the same as a control animal which was positive in an antibody with the same kit.

Besides, the liquid passed through the above column is passed through a column packed with guinea pig anti-HBe antibody carried on Sepharose CL 4B, by which only HBeAg is adsorbed thereon, and the HBeAg is isolated by eluting it with 0.1 M HCl-glycine buffer (pH 2.5).

In the same manner as described above, HBsAg is produced except that the culture liquid of the transformed COS cells are used instead of the culture liquid of the transformed mouse L cells, (LTK$^+$). The HBsAg thus obtained has the properties similar to those of HBsAg in human blood serum.

What is claimed is:

1. A recombinant DNA capable of replication in mammalian cells, which comprises 3 fragments of Hepatitis B virus subtype adr (HBV) DNA recombined with a vector, said vector comprising essentially of 0.31 Kb replication origin SV40 DNA inserted into the EcoRI cleavage site of *Escherichia coli* plasmid pBR322, wherein said plasmid is deficient in the 1.426–2.521 Kb region of inhibiting replication in mammalian cells and has an antibiotic resistant gene as a selective marker, wherein each of said HBV DNA fragments is comprised of a 3.2 Kb DNA having the BamHI site at both terminal ends, said BamHI DNA consisting of a 1.9 Kb HBc gene and a 1.3 Kb HBs gene, wherein said HBV DNA fragments are arranged in a head-to-tail tandem relationship wherein the HBc gene positions at the head and the HBs gene positions at the tail.

2. Recombinant DNA according to claim 1, having thymidine kinase DNA.

3. A mammalian cell transformed by recombinant DNA capable of replication in mammalian cells, wherein said recombinant DNA comprising 3 fragments of Hepatitis B virus subtype adr (HBV) DNA recombined with a vector said vector consisting essentially of 0.31 Kb replication origin SV40 DNA inserted into the EcoRI cleavage site of *Escherichia coli* plasmid pBR322, wherein said plasmid is deficient in the 1.426–2.521 Kb region of inhibiting replication in mammalian cells and has an antibiotic resistant gene as a selective marker, wherein each of said HBV DNA fragments is comprised of a 3.2 Kb DNA having the BamHI site at both terminal ends, said BamHI DNA consisting of a 1.9 Kb HBc gene and a 1.3 Kb HBs gene, wherein said HBV DNA fragments are arranged in a head-to-tail tandem relationship wherein the HBc gene positions at the head and the HBs gene positions at the tail.

4. The transformed mammalian cell of claim 3 wherein said mammalian cell is a thymidine kinase deficient mammalian cell.

5. The transformed mammalian cell of claim 3, wherein the mammalian cell is a mouse LTK$^-$ cell.

6. The transformed mammalian cell according to claim 3, wherein said mammalian cell is a COS cell.

7. The transformed mammalian cell according to claim 3, wherein said recombinant DNA includes thymidine kinase DNA.

8. A method for producing Hepatitis B virus subtype adr "e" antigen which comprises the steps of transforming a mammalian cell with recombinant DNA capable of replication in mammalian cells, wherein said recombinant DNA comprises 3 fragments of Hepatitis B virus subtype adr (HBV) DNA recombined with a vector said vector consisting essentially of 0.31 Kb replication origin SV40 DNA inserted into the EcoRI cleavage site of *Escherichia coli* plasmid pBR322, wherein said plasmid is deficient in the 1.426–2.521 Kb region of inhibiting replication in mammalian cells and has an antibiotic resistant gene as a selective marker, wherein each of said HBV virus DNA fragments is comprised of a 3.2 Kb DNA having the BamHI site at both terminal ends, said BamHI DNA consisting of a 1.9 Kb HBc gene and a 1.3 Kb HBs gene, wherein HBV DNA fragments are arranged in a head-to-tail tandem relationship wherein the HBc gene positions at the head and the HBs gene positions at the tail, incubating said transformed mammalian cells; and, collecting the produced Hepatitis B virus e antigen.

* * * * *